United States Patent
Wallace et al.

[11] Patent Number: 5,941,888
[45] Date of Patent: Aug. 24, 1999

[54] VASO-OCCLUSIVE MEMBER ASSEMBLY WITH MULTIPLE DETACHING POINTS

[75] Inventors: Michael P. Wallace, Pleasanton; Chad C. Roue, Livermore, both of Calif.

[73] Assignee: Target Therapeutics, Inc., Fremont, Calif.

[21] Appl. No.: 09/025,707

[22] Filed: Feb. 18, 1998

[51] Int. Cl.⁶ .................................................. A61B 17/00
[52] U.S. Cl. ........................................... 606/108; 606/200
[58] Field of Search ................................ 606/32, 41, 49, 606/28, 108, 191, 200

[56] References Cited

U.S. PATENT DOCUMENTS

| | | |
|---|---|---|
| 4,739,768 | 4/1988 | Engelson . |
| 4,884,575 | 12/1989 | Sanders . |
| 4,994,069 | 2/1991 | Ritchart et al. . |
| 5,067,491 | 11/1991 | Taylor, II et al. . |
| 5,122,136 | 6/1992 | Guglielmi et al. . |
| 5,174,295 | 12/1992 | Christian et al. . |
| 5,226,911 | 7/1993 | Chee et al. . |
| 5,250,071 | 10/1993 | Palermo . |
| 5,312,415 | 5/1994 | Palermo . |
| 5,354,295 | 10/1994 | Guglielmi et al. . |
| 5,380,320 | 1/1995 | Morris . |
| 5,382,259 | 1/1995 | Phelps et al. . |
| 5,423,829 | 6/1995 | Pham et al. . |
| 5,522,836 | 6/1996 | Palermo . |
| 5,540,680 | 7/1996 | Guglielmi et al. . |
| 5,569,245 | 10/1996 | Guglielmi et al. . |
| 5,624,449 | 4/1997 | Pham et al. . |

OTHER PUBLICATIONS

Sadato et al., "Treatment of a spontaneous carotid cavernous fistula using an electrodetachable microcoil" *American J. of Neuroradiology* (1993) 14:334–336.

*Primary Examiner*—Michael Buiz
*Assistant Examiner*—Vikki Trinh
*Attorney, Agent, or Firm*—Morrison & Foerster LLP

[57] ABSTRACT

This device is an apparatus for endovascular occlusion through the formation of thrombi in arteries, veins, aneurysms, vascular malformations, and arteriovenous fistulas. In particular, the device includes multiple vaso-occlusive members connected by electrolytically disintegratible links. Each link connects to the vaso-occlusive member by electrically insulative and conductive joints on opposite ends of the link. The vaso-occlusive members are delivered through a delivery catheter having on its distal end an electrode for electrical contact with the vaso-occlusive member. Upon application of an electrical current through electrode to the vaso-occlusive member and its conductive joint to electrolytically disintegratible link, the link disintegrates, selectively detaching the desired number of vaso-occlusive members into the target thrombus formation site.

37 Claims, 6 Drawing Sheets

VASO-OCCLUSIVE MEMBER ASSEMBLY WITH MULTIPLE DETACHING POINTS

FIELD OF THE INVENTION

This invention generally relates to the delivery of an occlusion device to a desired site in a mammal to facilitate the formation of mechanical blockage or thrombi in arteries, veins, aneurysms, vascular malformations and arteriovenous fistulas. More specifically, the invention involves one or more vaso-occlusive members that can be sequentially and selectively delivered by electrolytic detachment of a sacrificial link to a desired thrombus formation site. This invention permits a physician effectively to select the length of a vaso-occlusive device for delivery to a selected site without removing the delivery wire from the delivery catheter.

BACKGROUND OF THE INVENTION

Approximately 25,000 intracranial aneurysms rupture each year in North America. The primary purpose of treatment for a ruptured intracranial aneurysm is to prevent rebleeding. There are a variety of ways to treat ruptured and non-ruptured aneurysms.

Possibly the most widely known of these procedures is an extravascular approach using surgery or microsurgery. This treatment is common with intracranial berry aneurysms. The method comprises a step of clipping the neck of the aneurysm, performing a suture ligation of the neck, or wrapping the entire aneurysm. Each of these procedures is formed by intrusive invasion into the body and performed from the outside of the aneurysm or target site. General anesthesia, craniotomy, brain retraction, and placement of a clip around the neck of the aneurysm are typically required in these surgical procedures. The surgical procedure is often delayed while waiting for the patient to stabilize medically. For this reason, many patients die from the underlying disease or defect prior to the initiation of the procedure.

Another procedure—the extra-intravascular approach—involves surgically exposing or stereotactically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated by reference.

A still further approach is the least invasive and is additionally described in Guglielmi et al. It is the endovascular approach. In this approach, the interior of the aneurysm is entered by use of a catheter such as those shown in U.S. Pat. No. 4,884,575 and U.S. Pat. No. 4,739,768, both to Engelson. These patents describe devices utilizing core wires and catheters, respectively, which allow access to the aneurysm from remote portions of the body. By the use of catheters having very flexible distal regions and core wires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using catheters such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less favorable because of the difficulty in introducing the balloon into the aneurysm sac, the possibility of an aneurysm rupture due to overinflation of the balloon within the aneurysm, and the risk associated with the traction produced when detaching the balloon.

A highly desirable embolism-forming device which may be introduced into an aneurysm using endovascular placement procedures is found in U.S. Pat. No. 4,994,069, to Ritchart et al. The device, typically a platinum/tungsten alloy coil having a very small diameter, may be introduced into an aneurysm through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture. Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136) as discussed above.

Guglielmi et al. teaches an embolism-forming device and procedure for using that device. Specifically, Guglielmi et al. fills a vascular cavity such as an aneurysm with an embolic device such as a platinum coil which has been endovascularly delivered. The coil is then severed from its insertion tool by the application of a small electric current. Desirably, the insertion device involves a core wire which is attached at its distal end to an embolic device by an electrolytic, sacrificial joint. Guglielmi et al. suggests that when the embolic device is a platinum coil, the coil may have a length ranging from 1 cm to 50 cm or longer as is necessary. Proximal of the embolic coil is an insulated core wire or pusher wire, often stainless steel in construction. The core wire is used to push the platinum embolic coil, obviously with great gentleness, into the vascular site to be occluded. The Guglielmi et al. patent shows a variety of ways to link the embolic coil to the core wire. For instance, the core wire is tapered at its distal end and the distal tip of the core wire is welded into the proximal end of the embolic coil. Additionally, a stainless steel coil is wrapped coaxially about the distal tapered portion of the core wire to provide column strength to the core wire. This coaxial stainless steel wire is joined both to the core wire and to the embolic coil. Insulation may be used to cover a portion of the strength-providing stainless steel coil. This arrangement provides for two regions which must be electrolytically severed before the embolic coil is severed from the core wire.

A still further variation found in Guglielmi et al. includes a thin, threadlike extension between the core wire core and the proximal end of the embolic coil. In this way, the core wire does not extend to the embolic coil, but instead relies upon a separately introduced extension.

A continuation-in-part of the Guglielmi et al. patent discussed above, U.S. Pat. No. 5,354,295, describes the use of mechanically detachable embolic devices as well as those which are electrolytically detachable. The embolic devices may be augmented with attached filaments. U.S. Pat. No. 5,540,680, a continuation of U.S. Pat. No. 5,354,295, further describes such mechanically and electrolytically detachable embolic devices. U.S. Pat. No. 5,569,245, a continuation-in-part of the U.S. Pat. No. 5,540,680 patent, adds several new aspects including a new method for electrocoagulation.

A further variation of the Guglielmi et al. device is one in which the distal tip of the stainless steel core wire is crimped onto the proximal end of the embolic device. A simple tapered stainless steel wire extends from the stainless steel pusher wire to the embolic coil.

Taki et al. have devised a variation of the Guglielmi detachable coil using a copper link between the core wire and the coil, described in *Treatment of a Spontaneous Carotid Cavernous Fistula Using an Electrodetachable Microcoil*, American Journal of Neuroradiology, Vol. 14 (1993).

U.S. Pat. Nos. 5,423,829 to Pham et al. and 5,624,449 to Pham et al. describe an electrolytically detachable vaso-occlusive device containing a discrete sacrificial link between the core wire and the vaso-occlusive device to allow clean and quick detachment from the core wire, reducing the possibility of multiple electrolysis sites The use of extensive electrical insulation about the core wire and sacrificial link as well as the use of scoring on the insulation to focus electrolysis on a targeted, specific site on the link is also taught by Pham et al.

In order to tailor the length of the vaso-occlusive member during implantation so to effectively treat the aneurysm, U.S. Pat. No. 5,522,836 to Palermo discloses a vaso-occlusive device such as a coil in which the length of the coil can be tailored during the procedure. This is accomplished by the use of an electrode which is movable relative to the vaso-occlusive coil.

U.S. Pat. No. 5,312,415 to Palermo teaches another device that enables more accurate placement of a vaso-occlusive coil. In this device, a catheter having a constricted or feathered distal end to retain vaso-occlusive coils on a core wire, allowing the delivery of a number of coils loaded on one pusher, thereby eliminating the need to remove the core wire from the catheter and re-insert it between coil deliveries.

None of the disclosed devices suggests the use of a vascular occlusion member assembly in which multiple vaso-occlusive devices can be selectively detached via multiple electrolytically disintegratible links.

SUMMARY OF THE INVENTION

This invention is a device for forming a vascular occlusion at a selected site. Generally, the device comprises a vaso-occlusive member having an electrically insulative joint located proximally on the vaso-occlusive member, an electrolytically disintegratible link located proximally of the insulative joint, and an electrically conductive region, which may be a section of conductive vaso-occlusive material, proximal of the link which connects to an additional vaso-occlusive member. In conjunction with this assembly is a delivery catheter having an integral distal electrode configured for electrical contact with the electrically conductive region of the vaso-occlusive members. These vaso-occlusive members may be placed nose-to-tail. Upon application of electric current to the electrically conductive region, a nearby electrolytically disintegratible link disintegrates, releasing a portion of the assembly. The presence of multiple disintegratible links, typically separated from each other by insulative joints, allows the placement of a selected number of vaso-occlusive members into the therapeutic site as the physician chooses. An alternative variation utilizes two catheters, one for delivering one or more vaso-occlusive members, the other for deploying an electrode for electrolytically detaching the desired number of vaso-occlusive members by disintegrating one of the links.

DESCRIPTION OF THE INVENTION

An artery, vein, aneurysm, vascular malformation or arterial fistula is occluded through endovascular occlusion by the endovascular insertion of a vaso-occlusive member into the vascular cavity. Because of the unique design of the present invention, the appropriate length vaso-occlusive member or members can effectively be selected by the physician without removal of the delivery wire from the delivery catheter.

Figure 1:
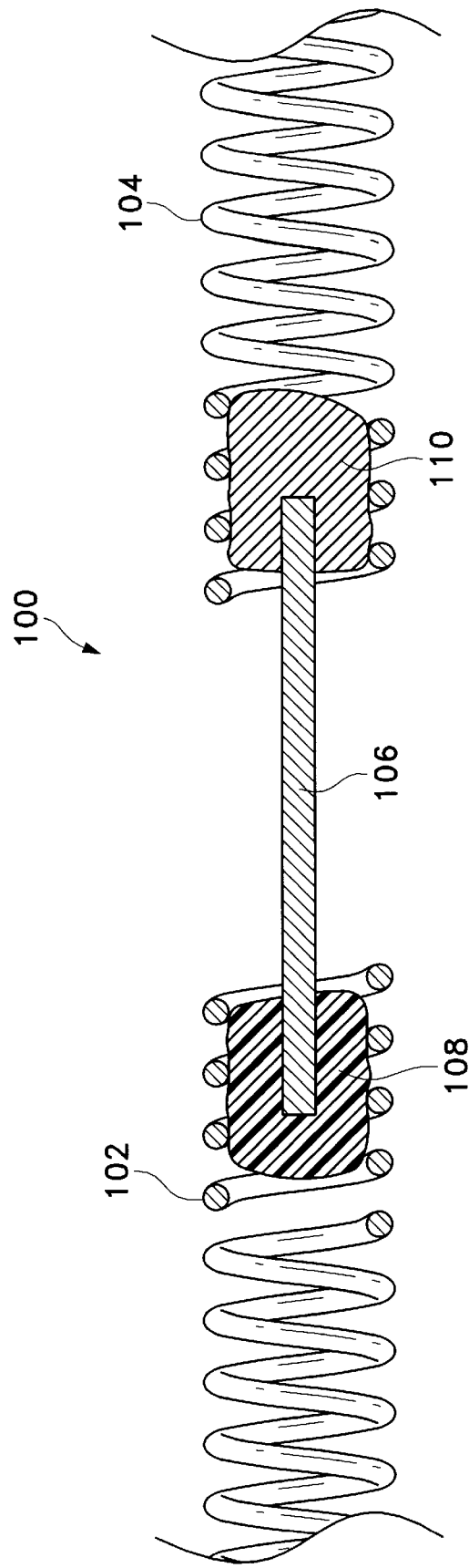
FIG. 1 is a cross-sectional view of one variation of the vaso-occlusive member assembly of the present invention.

FIG. 1 shows the basic vaso-occlusive assembly 100 of the present invention. The term "proximal" generally refers to the right side and the term "distal" generally refers to the left side of the figures in this document. Distal vaso-occlusive member 102 and proximal vaso-occlusive member 104 are shown as helical coils, although they may be any other suitable device or form, such as a ribbon, a braided member, or the like. Vaso-occlusive members 102 and 104 should be of a size sufficiently small that they may be advanced through a catheter (not shown) that is appropriately sized for accessing the targeted vascular site. For instance, when accessing a brain aneurysm in a small vessel, an appropriately sized catheter is quite small and very flexible. The vaso-occlusive member in such a situation must be small enough to fit through the catheter and out its distal end at the treatment site. Optionally, vaso-occlusive members 102 and 104 may be elongated, depending upon the form the vaso-occlusive member takes. For instance, if vaso-occlusive members 102 and 104 are in the form of coils as shown in FIG. 1, they may be elongated by containing an increased number of total windings from their proximal to distal ends. As shown in FIG. 1, vaso-occlusive assembly 100 can consist of multiple vaso-occlusive members 102 and 104. Additionally, assembly 100 may consist of any number of vaso-occlusive members, depending on the specific treatment desired by the physician.

Vaso-occlusive members 102 and 104 are desirably made up of a radiopaque, physiologically compatible material. Suitable metals and alloys for the wire making up those regions include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biocompatible. Highly preferred is a platinum/tungsten alloy, e.g., 8% tungsten and the remainder platinum.

Certain polymers are also suitable as vaso-occlusive member material either alone or in conjunction with metallic markers to provide radiopacity. These materials are chosen so that the procedure of locating the vaso-occlusive member within the vessel may be viewed using radiography. However, it is also contemplated that the vaso-occlusive members may be made of various other biocompatible polymers or of carbon fibers. The vaso-occlusive device may be covered or connected with fibrous materials tied to the outside of the coil or braided onto the outer cover of the coil as desired. Such fibrous adjuvants may be found in U.S. Pat. Nos. 5,354,295 to Guglielmi et al., 5,382,259 to Phelps et al., or in 5,226,911 to Chee et al., the entirety of which are incorporated by reference. The particular form of and choice of material used for the vaso-occlusive members will of course depend on the desired application. It is preferred that at least one of the vaso-occlusive members be electrically conductive so to make possible electrolytic separation of the assembly as will be described below.

When one or more of the vaso-occlusive members is a coil, its shape and constituent winding will depend upon the use to which the coil will be placed. For occluding peripheral or neural sites, the coils will typically be made of 1 mil to 5 mil diameter wire (platinum or platinum/tungsten alloy) that may be wound to have an inner diameter of 5 mils to 60 mils with a minimum pitch—that is to say that the pitch is equal to the diameter of the wire used in the coil. The outer diameter is then typically between 0.007 and 0.700 inch.

The length of the coil will normally be in the range of 0.5 to 60 cm, preferably 0.5 to 40 cm. As discussed in conjunction with FIG. 2 below, any number of vaso-occlusive devices may be used in the present invention, subject to considerations of safety, the length of the coils chosen, the therapy being administered by the attending physician, and the desire to maintaining the overall optimal stiffness of the vaso-occlusive member assembly. When, for instance, the vaso-occlusive members are coils, anywhere from two to twenty coils may be used, with a preferable number being two to ten, and an even more preferable number being two to five. Balancing the tendency for the overall stiffness of the joined coil assembly to increase with additional coils versus safety and other considerations is critical in determining the optimal number of coils or other vaso-occlusive members to be used in the present invention.

If desired, the coils may be formed in such a way that they are essentially linear as they pass through the catheter and yet assume a randomly oriented relaxed condition after they are released from the distal end of the catheter. A discussion of this variation may be found in U.S. Pat. No. 4,994,069 to Ritchart et al.

Electrolytically disintegratible link 106 is shown between vaso-occlusive members 102 and 104 in FIG. 1. Link 106 is preferably bare and is relatively more susceptible to electrolysis in an ionic solution such as blood or most other bodily fluids than is vaso-occlusive members 102 and 104. Alternatively, link 106 may be tapered or otherwise modified, or coated with an insulative polymer and scored, such as described in U.S. Pat. No. 5,624,449 to Pham et al., the entirety of which is incorporated by reference, to limit the area of electrolytic disintegration of link 106 to a more discrete region or point. For all figures herein, the electrolytically disintegratible link may take the form of a straight member (as shown in FIG. 1 for link 106), or may take the form of other shapes; for example, a coil. One advantage of having link 106 take the form of a coil is that this configuration would help preserve the uniform diameter of vaso-occlusive members 102 and 104.

Central to this invention is electrical isolation of vaso-occlusive members 102 and 104 by electrically insulative joint 108, which joins the proximal end of vaso-occlusive member 102 to link 106. Without wishing to be bound by theory, it is believed that electrical isolation of vaso-occlusive members 102 and 104 prevents or lessens current flow through the vaso-occlusive members and concentrates the current flow through link 106. Preferably, as shown in FIG. 1, insulative joint 108 surrounds link 106 and is contained within the lumen defined by vaso-occlusive member 102.

Insulative joint 108 serves two primary functions. The first is to electrically insulate link 106 from vaso-occlusive member 102 so that electrical energy is not transmitted from the link to vaso-occlusive member or any part of the assembly of the present invention distal to the particular link 106 selected for electrolytic disintegration. The second is to reliably and fixedly join link 106 to vaso-occlusive member 102.

Preferably, electrically insulative joint 108 is comprised of a biocompatible, electrically insulative material such as polyfluorocarbons (e.g. TEFLON), polyethylene terepthalate, polypropylene, polyurethane, polyimides, polyvinylchloride, and silicone polymers.

In addition to the polymers listed above, another desirable material is generically known as Parylene. There are a variety of polymers (,e.g., polyxylylene) based on para-xylylene. These polymers are typically placed onto a substrate by vapor phase polymerization of the monomer. Parylene N coatings are produced by vaporization of a di(P-xylylene) dimer, pyrolization, and condensation of the vapor to produce a polymer that is maintained at a comparatively lower temperature. In addition to Parylene-N, Parylene-C is derived from di(monochloro-P-xylylene) and Parylene-D is derived from di(dichloro-P-xylylene). There are a variety of known ways to apply Parylene to substrates. Their use in surgical devices has been shown, for instance, in U.S. Pat. No. 5,380,320 (to J. R. Morris), in U.S. Pat. No. 5,174,295 (to Christian et al.), in U.S. Pat. No. 5,067,491 (to Taylor et al.) and the like.

Alternatively, thermoplastic materials such as that disclosed in U.S. patent application Ser. No. 08/891,936, entitled CONTROLLED DETACHABLE VASOOCCLUSIVE MEMBER USING MECHANICAL JUNCTION AND FRICTION-ENHANCING MEMBER, the entirety of which is incorporated by reference, are contemplated for use as adhesives in comprising insulative joint 108 in the present invention, alone or in combination with the other polymers herein described.

The thermoplastic, polymer or combination of such used to comprise insulative joint 108 may be formed in any number of ways. One technique, for example, is dipping or coating link 106 in a molten or substantially softened polymer material, but other techniques as known in the art, such as shrink-wrapping, line-of-sight deposition in the form of a suspension or latex, or others may be used as well.

Another material that may be used for electrically resistive insulative joint 108, alone or in combination with one or more thermoplastic or polymer layer, is a biocompatible and electrically resistive metallic oxide. Oxides with a high dielectric constant, such as those of tantalum or titanium or their alloys, are preferred, with the various oxides of tantalum as most preferred. Such oxides can be formed in any number of ways. For example, they may be in the form of a deposited film, such as that made by plasma deposition of the base metal (e.g., in elemental or alloy form), or they may exist in the form of a sleeve or hypotube of the base metal that is welded, brazed, soldered, mechanically joined, or otherwise fixed to link 106. This base metal layer can then be subsequently oxidized (by imposition of the appropriate electrical current or other such excitation, such as by welding during assembly of the device) to form the desired electrically insulative oxide layer. Alternatively, the oxide may be deposited directly in oxide form by any number of techniques that does not require subsequent oxidation of the base metal in elemental or alloy form.

Whether electrically insulative joint 108 is comprised of a monolithic layer of a single polymer or thermoplastic, multiple layers of various polymers or thermoplastics, or an electrically insulative metallic oxide (alone or in combination with any number of polymers or thermoplastics), its thickness (as measured radially outward from the surface of link 106 towards vaso-occlusive member 102) can range from 0.002 inch to 0.040 inch, with 0.001 inch to 0.018 inch being preferred and 0.003 inch to 0.0010 inch as most preferred. It is preferred that the total thickness of insulative joint 108 be no greater than 0.060 inch (or, alternatively, no greater than the inner diameter of vaso-occlusive member 102) and no less than the minimum to allow insulative joint 108 to perform its intended functions of joining and electrically insulating vaso-occlusive member 102 and link 106.

The optimal thickness of each layer will depend on the desired thermal, electrical and mechanical properties of the insulative joint 108, the types and combinations of materials used, dimensional constraints relative to link 106 and vaso-occlusive member 102, and manufacturing, engineering, cost and other factors as well. For instance, the thickness of insulative joint 108 can range from one or a few hundred angstroms (for example if an oxide layer was used) to as thick as the remaining inner diameter of the vaso-occlusive member 102 (for example if a polymer or thermoplastic was used), taking into consideration the diameter of link 106, in which it is positioned. This latter thickness is especially desirable from a manufacturing standpoint as the insulative joint 108 most readily serves its two aforementioned functions of electrical insulation and joining.

Insulative joint 108 may join vaso-occlusive member 102 to link 106 by any number of various techniques. For example, joint 108 may be formed by an interference, or friction, fit. Alternatively, insulative joint 108 can be formed by line-of-sight deposition methods while link 106 and vaso-occlusive member 102 are aligned in the desired position so that as link material is deposited, it "fixes" the link 106 and vaso-occlusive member 102 into a locked position relative to one another.

Proximal of link 106, electrically conductive joint 110 joins the distal end of vaso-occlusive member 104 to link 106. Preferably, as shown in FIG. 1, conductive joint 110 surrounds link 106 and is contained within the lumen defined by vaso-occlusive member 104.

Conductive joint 110 serves two primary functions. The first is to provide an electrical pathway between link 106 from vaso-occlusive member 104 so that electrical current is readily transmitted between these two members. The second is to reliably and fixedly join link 106 to vaso-occlusive member 104.

Conductive joint 110 can be made from any biocompatible, electrically conductive material, preferably a suitable metal such as platinum or stainless steel hypotubing. In addition, a superelastic material such as nitinol may be used if desired; however, care must be taken in this case to keep it free from surface oxidation prior to fixing the joint 110 to the coil (such as by fabrication in a substantially oxygen-free environment or by plating the joint 110 with a conductive metal such as, for example, gold, silver, etc.). If conductive joint 110 comprises a stainless steel hypotube, the joint may be assembled by welding, brazing, soldering, mechanically joining (as by crimping, for example) or otherwise connecting a hypotube having a wall thickness appropriate to join link 106 and vaso-occlusive member 104 to proximal end of link 106. This hypotube is then welded, brazed, soldered, or otherwise fixed to vaso-occlusive member 104.

Figure 2:
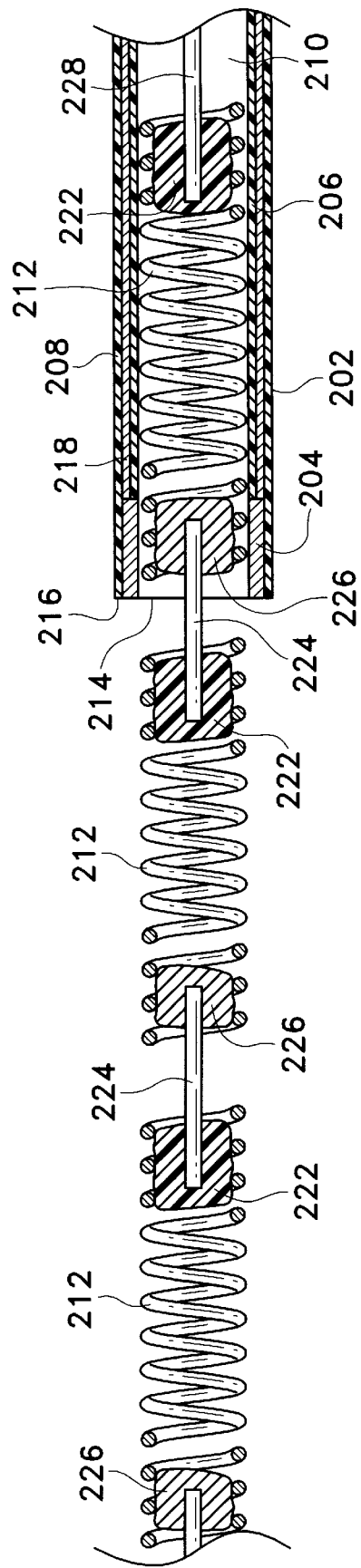
FIG. 2 is the vaso-occlusive member assembly in conjunction with a delivery catheter containing an electrode.

FIG. 2 shows, in partial cross-section, a series of vaso-occlusive members as described according to FIG. 1 in cooperation with the distal end of a catheter 202 having distal electrode 204 similar to that described in pending U.S. application Ser. No. 08/546,516, entitled DELIVERY CATHETER FOR ELECTROLYTICALLY DETACHABLE IMPLANT, the entirety of which is incorporated by reference.

Preferably, and as described in pending U.S. application Ser. No. 08/546,516, catheter 202 comprises an elongated tubular member or tube having a laminate structure comprising a pair of concentrically arranged tubular members or tubes 206 and 208. The inner surface or wall of first tube 206 defines lumen 210 through which the vaso-occlusive members, numbered generally as 212, are passed. Other catheter constructions may be used without departing from the scope of the invention.

Catheter 202 is preferably equipped with an annular distal electrode 204, partially embedded between first tube 206 and second tube 208, as shown in FIG. 2. Electrode 204 can be comprised of any conductive biocompatible material. For example, electrode 204 can be comprised of conductive metals and their alloys (for example, steel, titanium, copper, platinum, nitinol, gold, silver or alloys thereof), carbon (fibers or brushes), electrically conductive doped polymers or epoxies, or any combination thereof. In this variation, electrode 204 and tubes 206 and 208 are preferably designed so that the electrode 204 and catheter lumen 210 present a continuous, nonobstructed, smooth surface to allow vaso-occlusive member 212 to pass smoothly out of the distal end of catheter 202. Such an annular construction maximizes the electrode's exposed surface area so to increase current flow efficiencies by avoiding too large a current density passing therethrough. Finally, it is preferred in this variation that distal surface 214 of electrode 204 is substantially flush with the distal surface 216 of catheter 202. However, other configurations wherein the electrode 204 is spaced inwardly from the distal surface 216 of catheter 202 to eliminate or minimize interference with other vaso-occlusive members, as disclosed in pending U.S. application Ser. No. 08/546, 516, is also within the scope of this invention. In the case where electrode 204 is spaced inwardly, it is preferred that the maximum offset from the distal surface 216 of catheter 202 be the distance between electrolytically disintegratible links 224. Likewise, configurations in which electrode 204 is spaced outwardly from the distal surface 216 of catheter 202 to ensure conductive contact with vaso-occlusive member 212 may also be used.

Catheter 202 is further provided with a conductor 218. As shown in FIG. 2, conductor 218 is in the form of an annular extension of electrode 204. Alternatively, conductor 218 can be in the form of a wire or ribbon whose distal end is coupled, for example by welding, to electrode 204. Conductor 218 extends from electrode 204 between tubular members 206 and 208 to proximal end portion of catheter 202 where it can be electrically connected to a power supply either directly or with a lead as would be apparent to one of ordinary skill in the art.

Vaso-occlusive members 212 are as described above in conjunction with FIG. 1. Accordingly, each is provided on its proximal end with an electrically insulative joint 222 joining vaso-occlusive member 212 to electrolytically disintegratible link 224. Likewise, link 224 is affixed to the distal end of vaso-occlusive member 212 is electrically conductive joint 226 as described above. The most proximal of vaso-occlusive members 212, which in FIG. 2 is depicted as located within the lumen 210 of catheter 212, is connected to a core wire 228 via electrically insulative joint 222. This core wire 228 is used by the physician to advance the series of vaso-occlusive members 212 through the catheter lumen and to the desired therapeutic site as is well-known in the art.

Although the configuration of insulative joint 222 being distal to conductive joint 226, as shown in FIG. 2, is preferable, it is also within the scope of this invention to switch the respective locations of these elements so that insulative joint 222 lies proximal to conductive joint 226. In this latter alternative configuration, detachment will occur by electrolytic dissolution of a link 224 that is positioned proximal of electrode 204.

Figure 3:
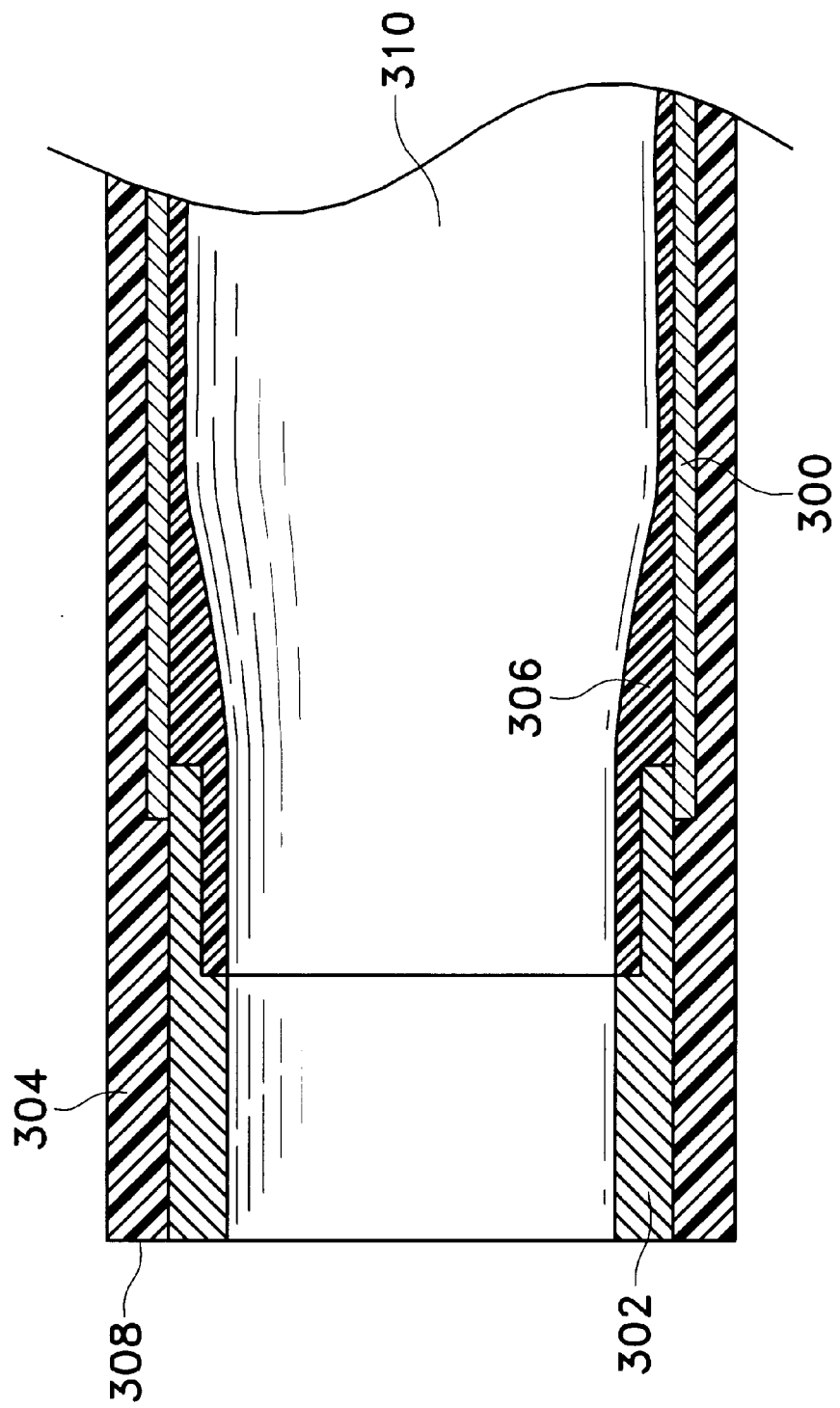
FIG. 3 is a cross-sectional view of the distal end of a catheter containing an alternative electrode arrangement.

An alternative electrode-catheter configuration is shown in FIG. 3. In this variation, conductor 300 is connected to, or can be an integral part of, electrode 302. Electrode 302 is partially covered and conductor 300 is completely covered on the inner diameter of catheter 304 with an electrically insulative covering 306. This covering serves to electrically isolate conductor 300 and all but a distal section of electrode 302 from the lumen of catheter 304, as well as to provide a continuous, nonobstructed, smooth surface to allow vaso-occlusive members (not shown) to pass smoothly out of the distal end 308 of catheter 304. Electrically insulative covering 306 may be comprised of an electrically insulative polymer or polymers as described above, and may additionally or singly comprise an electrically insulative metallic oxide such as tantalum oxide or the like. In this configuration, conductor 300 can, for example, be a metallic braid, while electrode 302 can, for example, be a platinum or platinum alloy hypotube. Of course, conductor 300 and electrode 302 can take other forms or configurations. Electrode 302 may also extend beyond the distal end 308 of catheter 304 to ensure electrical contact with vaso-occlusive members; likewise, electrode 302 may.

It is within the scope of this invention for the electrode to take on other forms, for example, a tubular braided structure such as described in pending U.S. application Ser. No. 08/546,516. A braided configuration has the advantage of allowing the designer to vary the stiffness of the catheter by varying the mesh size of the braid along the length of the catheter.

Although FIG. 3 shows electrode 302 to be substantially flush with the distal surface 308 of catheter 304, electrode 302 can be spaced inwardly from the distal surface 308 of catheter 304 to eliminate or minimize interference with other vaso-occlusive members. Likewise, electrode 302 can be spaced outwardly from the distal surface 308 of catheter 304 to ensure conductive contact with a vaso-occlusive member.

Figures 4A, 4B:
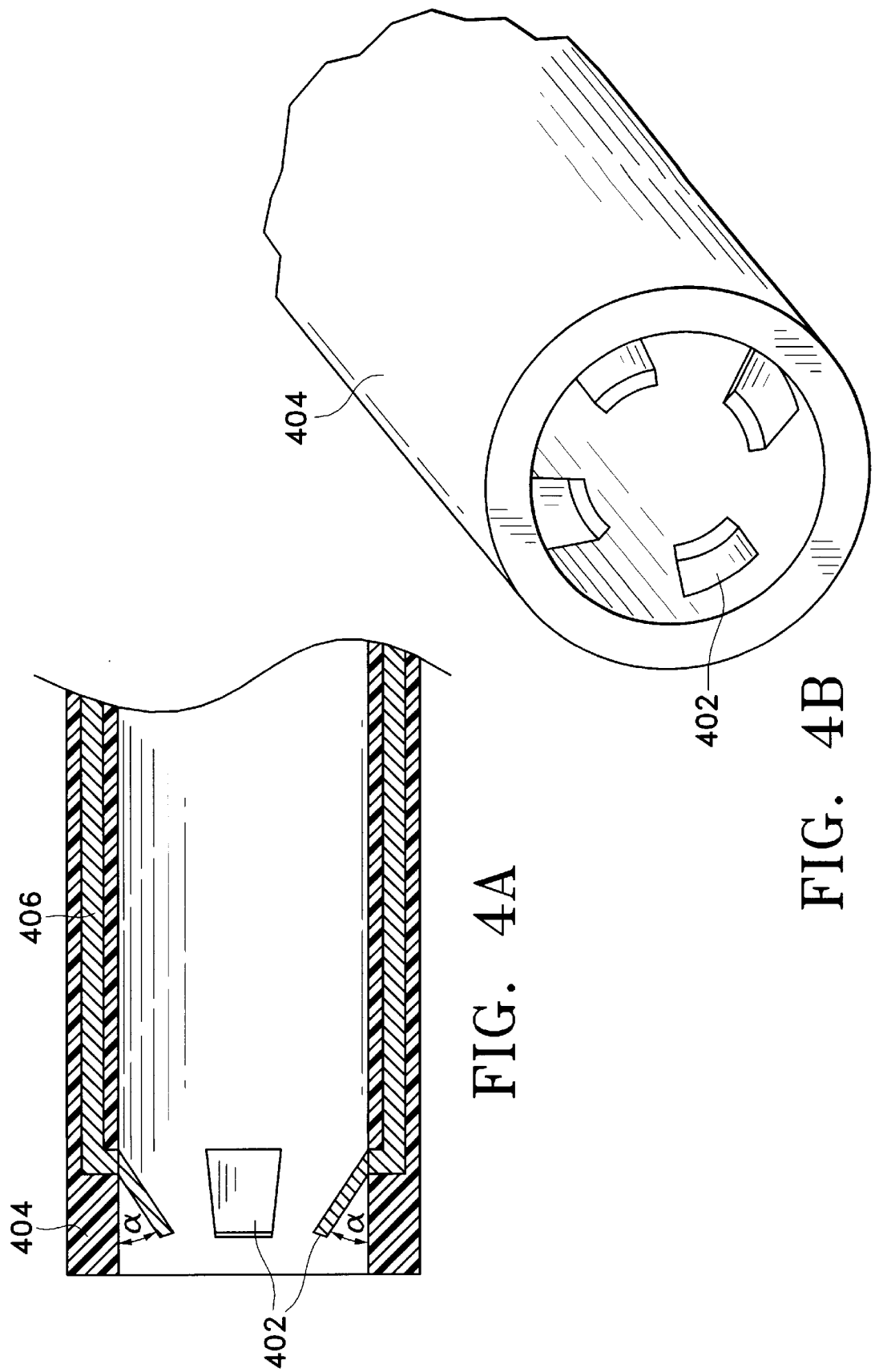
FIGS. 4A and 4B are cross-sectional and perspective views, respectively, of the distal end of a catheter containing another alternative electrode arrangement.

Turning now to FIGS. 4A and 4B, yet another variation of the electrode design which additionally accommodates vaso-occlusive members of different sizes is presented. In this configuration, the electrode consists of one or more radial extensions 402 located near the distal end of catheter 404. Radial extensions 402 extend radially towards the center of the catheter lumen from an electrically connected embedded conductor 406. Extensions 402 can be arranged symmetrically along the circumference of catheter 404 as shown in FIGS. 4A and 4B, or they may be arranged asymmetrically depending on the design of the invention. Although four extensions 402 are shown in FIGS. 4A and 4B, it is anticipated that from 1 to 10 extensions can exist in the distal end of catheter 404.

Extensions 402 can comprise any electrically conductive material, as discussed before, such as stainless steel, platinum, or nitinol, for example. It is important that extensions 402 be comprised of a material that has a relatively high degree of flexibility to allow passage of vaso-occlusive members (not shown) through the distal end of catheter 404 while being stiff enough to maintain electrical contact with the vaso-occlusive members so that electrical energy can be transmitted to the electrolytically disintegratible link (not shown).

Additionally, FIGS. 4A and 4B shows a preferred configuration for extensions 402. In this variation, extensions 402 are disposed at an acute angle a as measured from the catheter inner surface on the distal side of extension 402. This design facilitates passage of vaso-occlusive members out through the distal end of catheter 404 and into the therapeutic site, while simultaneously hindering motion in the opposite direction back into the lumen of catheter 404. It is contemplated that extensions 402 can be disposed at an angle α which is acute or even, in some cases, ninety degrees or slightly obtuse.

Extensions 402 can be in the form of ribbons, for example, that are welded, brazed, soldered, glued, or otherwise electrically and fixedly attached to conductor 406. Extensions 402 may also be an integral part of conductor 406. For example, extensions 402 can be cut from a nitinol hypotube on three sides and bent to the desired angle a on the still-intact fourth side which joins the hypotube. This hypotube can then be assembled with catheter 202. Alternatively, extensions 402 can be formed from one or more coils.

Figure 5:
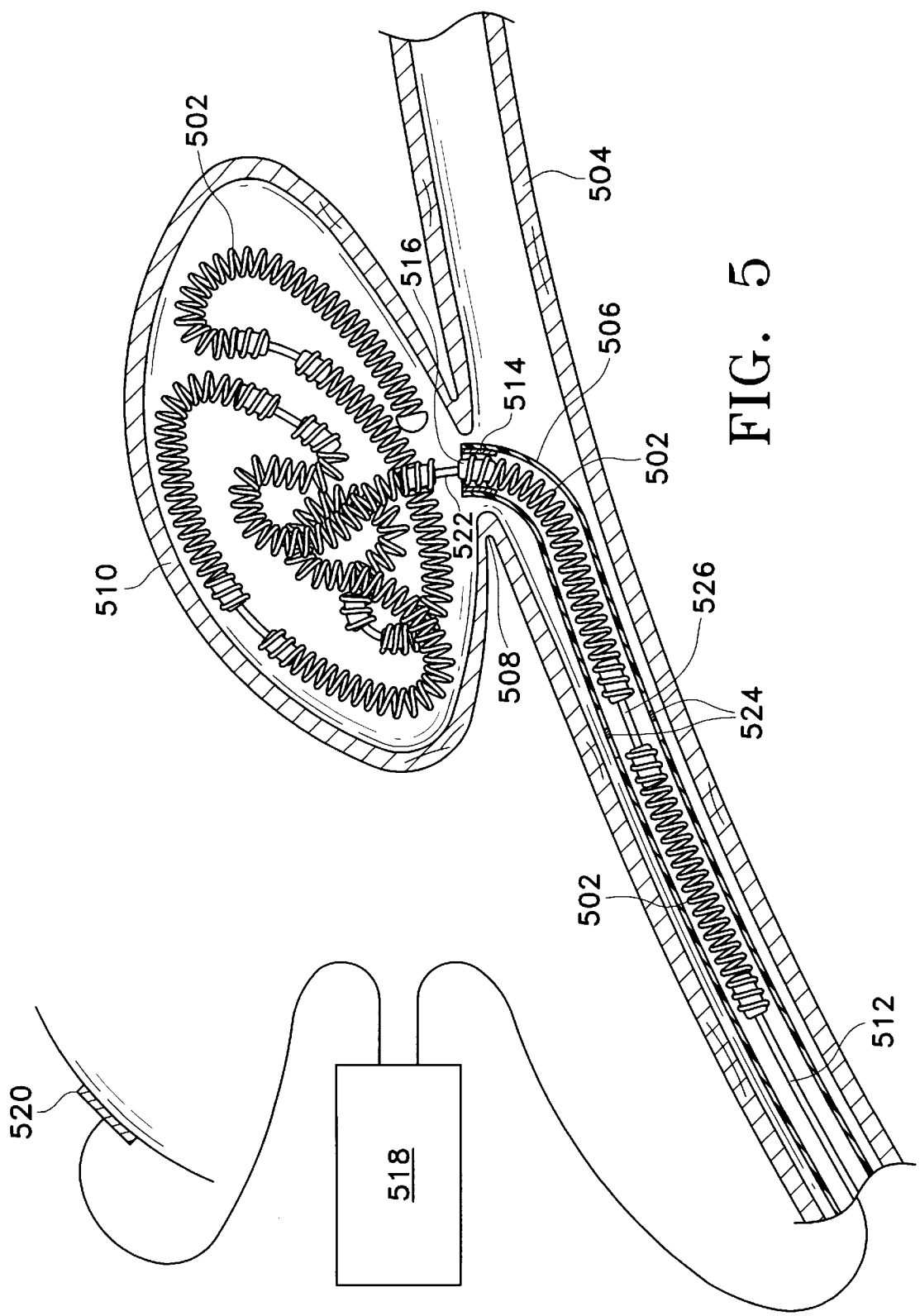
FIG. 5 schematically depicts the method of deploying the vaso-occlusive member assembly of the present invention into a vascular aneurysm.

FIG. 5 shows placement of a vaso-occlusive member 502 of the present invention within a vessel 504 with the distal end of catheter 506 placed near neck 508 of aneurysm 510. Conventional catheter insertion and navigational techniques involving core wires or flow-directed devices may be used to access the aneurysm 510. Once the distal end of catheter 506 is positioned at the site, often by locating its distal end through the use of radiopaque marker material and fluoroscopy, the catheter is cleared. For instance, if a core wire has been used to position the catheter, it is withdrawn from the catheter and then the core wire 512 having any number of vaso-occlusive members 502 at the distal end is advanced through the catheter. The core wire 512 is advanced so that the link 522 to be electrolytically severed is just outside the distal end of catheter 506 and is in electrical contact with the electrode 514 through conductive joint 516. To assist the physician in positioning the desired link 522 to be electrolytically detached, radiopaque marker 524 can be used. Because different occlusions, such as aneurysm 510, will require varying amounts of vaso-occlusive material for proper treatment, it may be necessary to deploy multiple vaso-occlusive members 522 into aneurysm 510. With the assistance of radiopaque marker 524, the physician can selectively deploy one or more vaso-occlusive member 502 into the aneurysm 510 as required until the aneurysm 510 has been sufficiently filled.

This marker 524, which is preferably comprised of a platinum hypotube, is embedded in catheter 506 and spaced proximally from the distal end of catheter 506 a distance that corresponds to the spacing between link 522 and link 526. Vaso-occlusive members 502 preferably are radiopaque while links 522 and 526 preferably are not.

When used in combination with electrode 514 (which can serve as or can additionally contain a radioopaque marker to indicate the distal end of catheter 504), a physician positions wire 512 so that link 526 is centered under radiopaque marker 524 as shown in FIG. 5. By doing so, the physician will know that the next most distal link 522 is positioned just distal of electrode 514 (through conductive joint 516) and that electrolytic detachment will occur at distal link 522.

Depending on constraints such as the condition and size of the occlusion, the physician may desire to use vaso-occlusive members 502 of varying length. Therefore, it is contemplated that catheter 504 can contain multiple radiopaque markers 524, each positioned in from the distal end of catheter 504 a distance corresponding to the spacing between links that separate vaso-occlusive members of varying length. This will give the physician maximum flexibility in accurately, reliably, and safely deploying any number of vaso-occlusive members of identical or varying lengths, singly or in combination, into the site to be occluded.

A positive electric current of approximately 0.01 to 2 milliamps at 0.1 to 6 volts is next applied to core wire 512 by power supply 518 to form a thrombus within aneurysm 510. Typically, the negative pole 520 of power supply is placed in electrical contact with the skin.

After the thrombus has been formed and the aneurysm occluded, link 522 just distal of electrode 514 is electrolytically disintegrated, detaching the desired number of vaso-occlusive devices from core wire 512.

After link 522 is completely dissolved or eroded by electrolytic action, typically within 0.5 to 10 minutes, the core wire 512 and catheter 506 are removed from vessel 504, leaving aneurysm 510 occluded.

Figure 6:
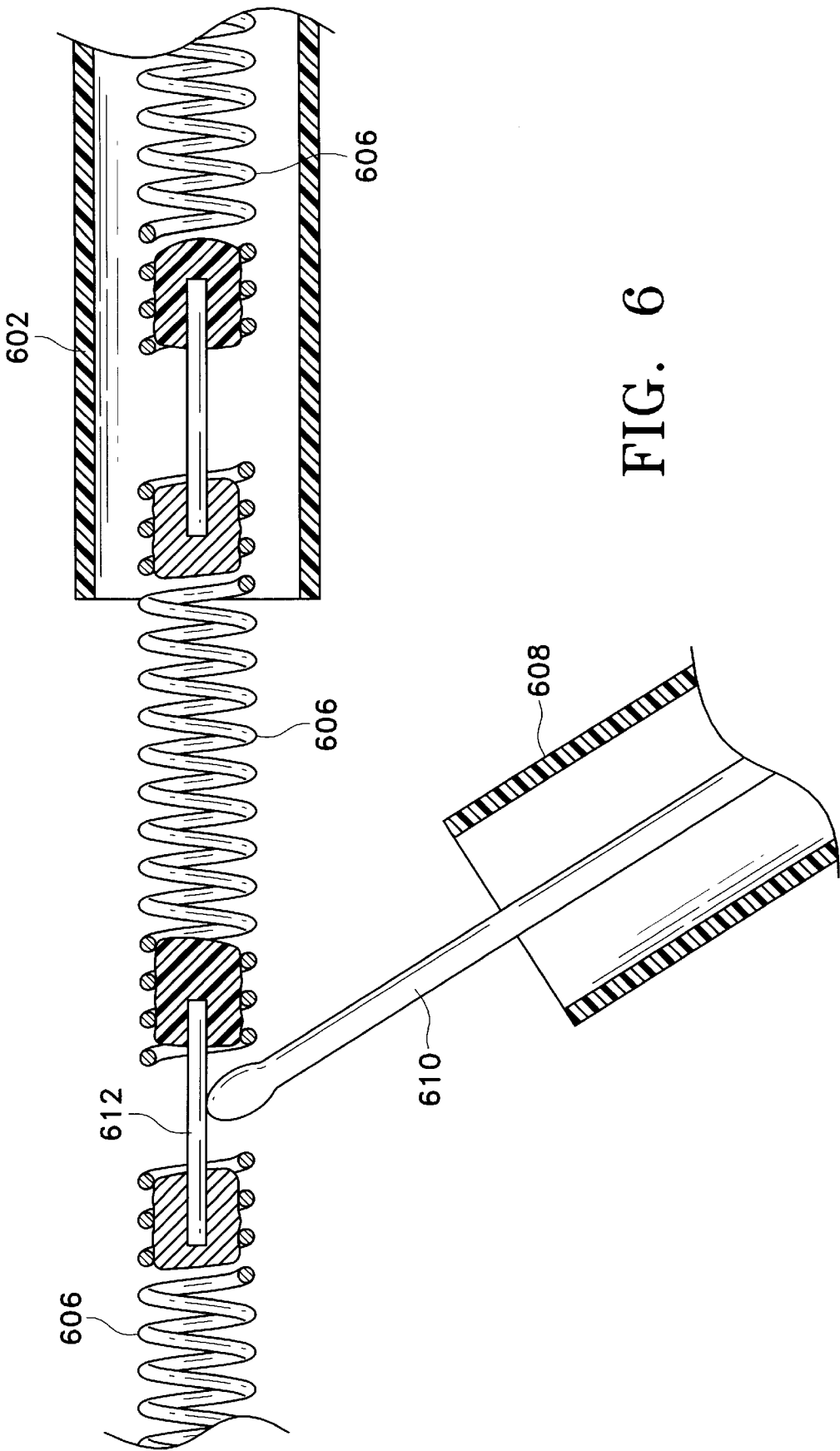
FIG. 6 is an alternative variation of the present invention in which a second catheter containing an electrode is used for detaching the vaso-occlusive member.

Finally, FIG. 6 illustrates an alternative variation of the inventive device as used in a mammal vasculature (not shown). In this configuration, catheter 602 containing core wire (not shown) and vaso-occlusive member 606 does not contain an electrode. A second microcatheter 608 containing an electrode 610 is used to access an exposed electrolytically disintegratible link 612 or vaso-occlusive member 606 to electrolytically disintegrate link 612 and detachment of the desired number of vaso-occlusive members 606 into the therapeutic site.

Although shown in FIG. 6 as an elongated wire, electrode 610 may take any number of forms as long as it effectively transmits electric current to a vaso-occlusive member 606 or link 612. Additionally, although first catheter 602 is shown in FIG. 6 as not having an electrode, this is not required. For example, a dual-catheter system in which the first catheter 602 contains an electrode that has become inoperative is within the scope of the invention.

Many alterations and modifications may be made by those having ordinary skill in the art without departing from the spirit and scope of the invention. The illustrated variations have been used only for illustration and clarity and should not be taken as limiting the invention as defined by the following claims.

We claim:

1. An assembly for use in the formation of an occlusion comprising:

a vaso-occlusive member having a proximal end and a distal end, an electrically insulative joint located proximally on said vaso-occlusive member, an electrolytically disintegratible link located proximally of said electrically insulative joint, and an electrically conductive joint located proximally on said electrolytically disintegratible link and distally on an additional vaso-occlusive member.

2. The assembly of claim 1 where at least one of said vaso-occlusive members is a coil.

3. The assembly of claim 1 where the electrically insulative joint comprises an electrically insulative biocompatible adhesive.

4. The assembly of claim 1 where the electrically insulative joint comprises an biocompatible oxide of a biocompatible metal.

5. The assembly of claim 4 where the biocompatible metal is tantalum.

6. The assembly of claim 1 where the electrically insulative joint comprises at least one polymer.

7. The assembly of claim 6 where the polymer is selected from the group consisting of polyfluorocarbons, polyxylylene, polyethylene, polyethylene terepthalate, polypropylene, polyurethane, polyimides, and silicone polymers.

8. The assembly of claim 6 where the electrically insulative joint additionally comprises an electrically insulative biocompatible adhesive.

9. The assembly of claim 6 where the electrically insulative joint additionally comprises a biocompatible oxide of a biocompatible metal.

10. The assembly of claim 9 where the biocompatible metal is tantalum.

11. The assembly of claim 1 where the electrically conductive end of the link comprises a hypotube.

12. An assembly for use in the formation of a vascular occlusion comprising:

a proximal section comprising a core wire having a proximal end and a distal end, a first electrically insulative joint attached to the distal end of said core wire, and a first vaso-occlusive member attached to said first electrically insulative joint, one or more distal sections, each comprising an electrically conductive joint attached to a distal electrolytically disintegratible link, an additional electrically insulative joint located distally on said electrically disintegratible link, and an additional distal vaso-occlusive member, and a catheter having a proximal end and a distal end and having an electrode configured for electrical contact with one of said vaso-occlusive members, whereby upon application of electrical current to a distal section, one of said electrolytically disintegratible links disintegrates, releasing a portion of said assembly.

13. The assembly of claim 12 where at least one of said vaso-occlusive members is a coil.

14. The assembly of claim 12 where the electrically insulative joint comprises an electrically insulative biocompatible adhesive.

15. The assembly of claim 12 where the electrically insulative joint comprises an electrically insulative oxide of a biocompatible metal.

16. The assembly of claim 15 where the biocompatible metal is tantalum.

17. The assembly of claim 12 where the electrically insulative joint comprises at least one polymer.

18. The assembly of claim 17 where the polymers are selected from the group consisting of polyfluorocarbons, polyxylylene, polyethylene, polyethylene terepthalate, polypropylene, polyurethane, polyimides, and silicone polymers.

19. The assembly of claim 17 where the electrically insulative joint comprises an electrically insulative biocompatible adhesive.

20. The assembly of claim 17 where the electrically insulative joint additionally comprises an electrically insulative oxide of a biocompatible metal.

21. The assembly of claim 17 where the biocompatible metal is tantalum.

22. The assembly of claim 12 where the electrically conductive insulative joint comprises a hypotube.

23. The assembly of claim 12 where said catheter additionally comprises at least two radiopaque markers.

24. The assembly of claim 23 where the distance between at least two of said radiopaque markers substantially equals the distance between said electrolytically disintegratible link and a second electrolytically disintegratible link.

25. The assembly of claim 12 where an electrically conductive extension of the electrode extends radially towards the center of the catheter and is in electrical contact with the vaso-occlusive member.

26. The assembly of claim 25 where the electrode extension is configured to allow passage of the vaso-occlusive member through the catheter in a direction from the proximal end towards the distal end and to simultaneously hinder passage of the vaso-occlusive member through the catheter in the opposite direction while maintaining the electrical contact with the vaso-occlusive member.

27. An assembly for use in the formation of a vascular occlusion, comprising:

a proximal section comprising a core wire having a proximal end and a distal end, a first electrically insulative joint attached to the distal end of said core wire, and a first vaso-occlusive member attached to said first electrically insulative joint, one or more distal sections, each comprising an electrically conductive joint attached to a distal electrolytically disintegratible link, an additional electrically insulative joint located distally on said electrically disintegratible link, and an additional distal vaso-occlusive member, a first catheter for delivering said proximal and distal sections to a desired vascular occlusion site, and a second catheter having an electrode configured for electrical contact with one of said vaso-occlusive members, whereby upon application of electrical current to said assembly, one of said electrolytically disintegratible links disintegrates, releasing a portion of said assembly.

28. The assembly of claim 27 where at least one of said vaso-occlusive members is a coil.

29. The assembly of claim 27 where the electrically insulative joint comprises an electrically insulative biocompatible adhesive.

30. The assembly of claim 27 where the electrically insulative joint comprises an oxide of a biocompatible metal.

31. The assembly of claim 30 where the biocompatible metal is tantalum.

32. The assembly of claim 27 where the electrically insulative joint comprises at least one polymer.

33. The assembly of claim 32 where the polymers are selected from the group consisting of polyfluorocarbons, polyxylylene, polyethylene, polyethylene terepthalate, polypropylene, polyurethane, polyimides, and silicone polymers.

34. The assembly of claim 32 where the electrically insulative joint comprises an electrically insulative biocompatible adhesive.

35. The assembly of claim 32 where the electrically insulative joint additionally comprises an electrically insulative oxide of a biocompatible metal.

36. The assembly of claim 32 where the biocompatible metal is tantalum.

37. The assembly of claim 27 where the electrically conductive insulative joint comprises a hypotube.

* * * * *